US009351721B2

(12) United States Patent
Auerbach et al.

(10) Patent No.: US 9,351,721 B2
(45) Date of Patent: May 31, 2016

(54) SUTURE PASSERS AND RELATED METHODS

(71) Applicant: CooperSurgical, Inc., Trumbull, CT (US)

(72) Inventors: Robert D. Auerbach, Madison, CT (US); Charles Sherts, Westport, CT (US)

(73) Assignee: CooperSurgical, Inc., Trumbull, CT (US)

( * ) Notice: Subject to any disclaimer, the term of this patent is extended or adjusted under 35 U.S.C. 154(b) by 345 days.

(21) Appl. No.: 13/735,143

(22) Filed: Jan. 7, 2013

(65) Prior Publication Data

US 2013/0218175 A1 Aug. 22, 2013

Related U.S. Application Data

(60) Provisional application No. 61/599,460, filed on Feb. 16, 2012.

(51) Int. Cl.
*A61B 17/04* (2006.01)
*A61B 17/06* (2006.01)
*A61B 17/00* (2006.01)

(52) U.S. Cl.
CPC ....... *A61B 17/0483* (2013.01); *A61B 17/06109* (2013.01); *A61B 2017/00424* (2013.01);
(Continued)

(58) Field of Classification Search
CPC ............... A61B 17/0483; A61B 17/06109; A61B 2017/00433; A61B 2017/06042; A61B 2017/00637; A61B 2017/0483; A61B 2017/0042
USPC .......... 606/145, 148, 205, 206, 139, 142, 144
See application file for complete search history.

(56) References Cited

U.S. PATENT DOCUMENTS

| 4,923,461 A | 5/1990 | Caspari et al. |
| 5,053,041 A | 10/1991 | Ansari et al. |

(Continued)

FOREIGN PATENT DOCUMENTS

| WO | WO9414381 | 7/1994 | |
| WO | WO 2012/034131 | 3/2012 | ............. A61B 17/04 |
| WO | WO 2012/939094 | 7/2012 | ............. A61B 17/04 |

OTHER PUBLICATIONS

International Search Report and the Written Opinion of the International Searching Authority for International Application No. PCT/US2013/020459 dated Jul. 23, 2013 (14 pages).

(Continued)

*Primary Examiner* — Ryan J Severson
*Assistant Examiner* — Anh Dang
(74) *Attorney, Agent, or Firm* — Fish & Richardson P.C.

(57) ABSTRACT

A suture passer includes an elongate tube defining a central lumen and having a beveled distal end region and a grasping member comprising a first elongate member and a first jaw extending distally from the first elongate member. The grasping member is sized to be disposed within the elongate tube and is capable of being extended from the elongate tube in a manner such that the first elongate member and the first jaw are disposed at least partially distal to the beveled distal end region of the elongate tube. The grasping member is further capable of being retracted within the elongate tube in a manner such that the first elongate member is located substantially within the central lumen of the elongate tube and the first jaw substantially covers an opening of the beveled distal end region of the elongate tube.

31 Claims, 18 Drawing Sheets

(52) U.S. Cl.
CPC ............... *A61B2017/00433* (2013.01); *A61B 2017/00637* (2013.01); *A61B 2017/00663* (2013.01); *A61B 2017/06042* (2013.01)

(56) References Cited

U.S. PATENT DOCUMENTS

| | | | |
|---|---|---|---|
| 5,059,201 A | 10/1991 | Asnis | |
| 5,261,917 A | 11/1993 | Hasson et al. | |
| 5,312,423 A | 5/1994 | Rosenbluth et al. | |
| 5,318,528 A | 6/1994 | Heaven et al. | |
| 5,364,410 A | 11/1994 | Failla et al. | |
| 5,387,227 A | 2/1995 | Grice | |
| 5,405,354 A | 4/1995 | Sarrett | |
| 5,431,666 A | 7/1995 | Sauer et al. | |
| 5,454,823 A | 10/1995 | Richardson et al. | |
| 5,458,609 A | 10/1995 | Gordon et al. | |
| 5,462,560 A | 10/1995 | Stevens | |
| 5,474,543 A | 12/1995 | McKay | |
| 5,496,335 A | 3/1996 | Thomason et al. | |
| 5,499,991 A | 3/1996 | Garman et al. | |
| 5,501,692 A | 3/1996 | Riza | |
| D368,776 S | 4/1996 | Toy et al. | |
| 5,569,269 A | 10/1996 | Hart et al. | |
| 5,591,179 A | 1/1997 | Edelstein | |
| 5,618,290 A | 4/1997 | Toy et al. | |
| 5,649,939 A | 7/1997 | Reddick | |
| 5,653,716 A | 8/1997 | Malo et al. | |
| 5,662,663 A | 9/1997 | Shallman | |
| 5,665,100 A | 9/1997 | Yoon | |
| 5,676,675 A | 10/1997 | Grice | |
| 5,749,879 A | 5/1998 | Middleman et al. | |
| 5,772,672 A | 6/1998 | Toy et al. | |
| 5,779,719 A | 7/1998 | Klein et al. | |
| 5,817,111 A | 10/1998 | Riza | |
| 5,817,112 A | 10/1998 | Christoudias | |
| 5,827,299 A | 10/1998 | Thomason et al. | |
| 5,910,148 A | 6/1999 | Reimels et al. | |
| 5,928,250 A | 7/1999 | Koike et al. | |
| 6,022,360 A | 2/2000 | Reimels et al. | |
| 6,074,403 A | 6/2000 | Nord | |
| 6,113,610 A | 9/2000 | Poncet | |
| 6,143,004 A | 11/2000 | Davis et al. | |
| 6,517,552 B1 | 2/2003 | Nord et al. | |
| 6,716,224 B2 | 4/2004 | Singhatat | |
| 6,921,408 B2 | 7/2005 | Sauer | |
| 7,169,156 B2 | 1/2007 | Hart | |
| 7,211,089 B2 | 5/2007 | Kear et al | |
| 7,731,723 B2 | 6/2010 | Kear et al. | |
| 7,766,937 B2 | 8/2010 | Ravikumar | |
| 8,133,255 B2 | 3/2012 | Ravikumar | |
| 8,328,824 B2 | 12/2012 | Hart | |
| 2001/0031984 A1 | 10/2001 | Hart | |
| 2003/0153928 A1 | 8/2003 | El-Galley | |
| 2003/0208100 A1 | 11/2003 | Levy | |
| 2004/0087978 A1 | 5/2004 | Velez et al. | |
| 2006/0020274 A1 | 1/2006 | Ewers et al. | |
| 2006/0069399 A1 | 3/2006 | Weisel et al. | |
| 2007/0016249 A1 | 1/2007 | Reznik | |
| 2007/0038230 A1 | 2/2007 | Stone et al. | |
| 2007/0118152 A1 | 5/2007 | Page | |
| 2007/0142744 A1 | 6/2007 | Provencher | |
| 2007/0156172 A1 | 7/2007 | Alvarado | |
| 2008/0097481 A1 | 4/2008 | Schorr et al. | |
| 2008/0319459 A1 | 12/2008 | Al-najjar | |
| 2009/0069824 A1 | 3/2009 | Chu | |
| 2009/0082788 A1 | 3/2009 | ElMaraghy | |
| 2010/0191260 A1 | 7/2010 | Mohajer | |
| 2010/0198235 A1 | 8/2010 | Pierce et al. | |
| 2011/0060350 A1 | 3/2011 | Powers et al. | |
| 2011/0306990 A1 | 12/2011 | Darois et al. | |
| 2012/0271323 A1 | 10/2012 | Fan et al. | |
| 2012/0277767 A1 | 11/2012 | Powers et al. | |
| 2012/0303046 A1 | 11/2012 | Stone et al. | |

OTHER PUBLICATIONS

International Preliminary Report on Patentability and Written Opinion for International Application No. PCT/US2013/020459 dated Aug. 28, 2014 (9 pages).

SUTURE PASSERS AND RELATED METHODS

CROSS-REFERENCE TO RELATED APPLICATIONS

This application claims the benefit of U.S. Provisional Application Ser. No. 61/599,460, filed on Feb. 16, 2012.

TECHNICAL FIELD

This disclosure relates to suture passers and related methods.

BACKGROUND

Suture passers are medical devices that can be inserted through a surgical wall (e.g., an abdominal wall) and then used to release a suture in a surgical cavity (e.g., a peritoneal cavity) or retrieve a suture from the surgical cavity. Suture passers are often used to repair a wound within the surgical wall following a surgical procedure. Such a wound can, for example, be formed by an endoscopic port during an endoscopic surgical procedure. To repair a wound, a suture passer is typically loaded with a suture and inserted through the surgical wall and into the surgical cavity at a point adjacent one side of the wound in order to deliver a suture into the surgical cavity. The suture is then released from the suture passer, and the suture passer is removed from the surgical wall. The suture passer is subsequently reinserted through the surgical wall and into the surgical cavity at a point adjacent the opposite side of the wound in order to grasp a portion of the suture located within the surgical cavity. The suture passer and the grasped suture are then removed from the surgical wall so that the suture can be tied off to close the wound.

SUMMARY

In one aspect of the invention, a suture passer includes an elongate tube defining a central lumen, where the elongate tube has a beveled distal end region. The suture passer further includes a grasping member including a first elongate member and a first jaw extending distally from the first elongate member, where the grasping member is sized to be disposed within the elongate tube. The grasping member is capable of being extended from the elongate tube in a manner such that the first elongate member and the first jaw are disposed at least partially distal to the beveled distal end region of the elongate tube, the grasping member is capable of being retracted within the elongate tube in a manner such that the first elongate member is located substantially within the central lumen of the elongate tube and the first jaw substantially covers an opening of the beveled distal end region of the elongate tube.

In another aspect of the invention, a method includes passing a suture passer through a surgical wall. The suture passer includes an elongate tube and a grasping member disposed within the elongate tube, where the grasping member is configured to substantially cover an opening of the elongate tube in a manner such that coring of the surgical wall is prevented as the suture passer is passed through the surgical wall. The method further includes grasping a suture with the grasping member and withdrawing the suture passer from the surgical wall while the suture is grasped by the grasping member.

Embodiments can include one or more of the following features.

In some embodiments, the first jaw covers about 80% to about 95% of an area of the opening.

In certain embodiments, the opening has an elliptical shape.

In some embodiments, the first jaw has a substantially elliptical shape, such that the first jaw substantially covers the opening while the grasping member is retracted within the elongate tube.

In certain embodiments, the beveled distal end region of the elongate tube includes a proximal edge and a distal edge.

In some embodiments, the first jaw includes a first edge and a second edge, where the first edge is aligned substantially flush with the distal edge of the beveled distal end region of the elongate tube when the grasping member is retracted within the elongate tube, and the second edge protrudes distally from the proximal edge of the beveled distal end region of the elongate tube when the grasping member is retracted within the elongate tube.

In certain embodiments, the second edge of the first jaw prevents the proximal edge of the elongate tube from coring a surgical wall as the suture passer is passed through the surgical wall.

In some embodiments, the second edge protrudes distally from the proximal edge of the beveled distal end region by about 0 inch to about 0.050 inch.

In certain embodiments, the suture passer further includes a second elongate member and a second jaw extending distally from the second elongate member.

In some embodiments, the first and second jaws cooperate to cover the opening when the grasping member is retracted within the elongate tube.

In certain embodiments, the first and second jaws cover about 80% to about 95% of an area of the opening when the grasping member is retracted within the elongate tube.

In some embodiments, the first and second elongate members are laterally spaced apart.

In certain embodiments, the first and second elongate members are configured such that a suture can be captured between the first and second elongate members when the grasping member is retracted within the elongate tube.

In some embodiments, the first elongate member includes a first bend from which the first jaw extends, the second elongate member includes a second bend from which the second jaw extends, and the first bend is longitudinally spaced from the second bend.

In certain embodiments, the first and second bends are arranged such that the first jaw contacts a central region of the second jaw when the grasping member is retracted within the elongate tube.

In some embodiments, the first bend is spaced about 0.05 inch to about 0.125 inch from the second bend.

In certain embodiments, the first bend has a first bend radius, the second bend has a second bend radius, and the first bend radius is different than the second bend radius.

In some embodiments, either or both of the first and second bend radii are about 0.050 inch to about 0.125 inch.

In certain embodiments, a peripheral edge of the first jaw is spaced from an inner surface of the elongate tube by about 0.005 inch to about 0.020 inch.

In some embodiments, a space between the peripheral edge and the inner surface of the elongate tube is less than a thickness of a suture to be carried by with the suture passer.

In certain embodiments, the grasping member further includes a base connected to a proximal end of the first elongate member.

In some embodiments, the base and the first elongate member are formed from a unitary structure.

In certain embodiments, the suture passer further includes an internal rod disposed within the central lumen of the elongate tube and coupled to the grasping member.

In some embodiments, the suture passer further includes a plunger assembly coupled to a proximal end of the internal rod, where the plunger assembly is operable to extend the grasping member from the beveled distal end region of the elongate tube.

In certain embodiments, the plunger assembly is operable to retract the grasping member within the central lumen of the elongate tube.

In some embodiments, the plunger assembly includes a button, a plunging member, and a spring surrounding the plunging member.

In certain embodiments, the plunger assembly is spring-loaded such that the grasping member is retracted within the elongate tube while the button is released and the spring is extended, and the grasping member is extended distally from the beveled distal end region of the elongate tube while the button is depressed and the spring is compressed.

In some embodiments, the grasping member has a length of about 1.25 inches to about 8.5 inches.

In certain embodiments, the suture passer has a length of about 9 inches to about 11 inches.

In some embodiments, the elongate tube has an outer diameter of about 0.060 inch to about 0.125 inch.

In certain embodiments, the elongate tube has an inner diameter of about 0.050 inch to about 0.110 inch.

In some embodiments, the elongate tube has a beveled distal end region having a proximal edge and a distal edge, and the grasping member is configured to prevent the proximal edge from coring the surgical wall as the suture passer is passed through the surgical wall.

In certain embodiments, the grasping member includes a jaw that extends distally beyond the proximal edge of the beveled distal end region.

In some embodiments, the grasping member includes an elongate member and a jaw extending distally from the elongate member, where the grasping member is configured to be extended distally from the elongate tube and to be retracted within the elongate tube.

In certain embodiments, grasping the suture comprises securing the suture between the jaw and an inner surface of the elongate tube.

In some embodiments, a peripheral edge of the jaw is spaced from an inner surface the elongate tube by about 0.005 inch to about 0.020 inch.

In certain embodiments, grasping the suture includes extending the grasping member from the elongate tube, positioning the grasping member adjacent the suture, and retracting the grasping member.

In some embodiments, withdrawing the suture passer from the surgical wall causes an end of the suture to be pulled outside of the surgical wall.

In certain embodiments, the surgical wall is an abdominal wall.

Embodiments can include one or more of the following advantages.

In some embodiments, a retracted configuration of the grasping member substantially prevents coring of the surgical wall as the suture passer is passed through the surgical wall. A jaw of the grasping member can, for example, be sufficiently sized and shaped such that the jaw substantially covers or closes the opening of the elongate tube while the grasping member is retracted within a distal end region of the elongate tube. When the grasping member is retracted within the elongate tube, an edge of the jaw protrudes slightly from the proximal edge of the beveled distal end region of the elongate tube. The slight protrusion of the edge of the jaw prevents the proximal edge of the beveled distal end region of the elongate tube from substantially piercing the surgical wall and thus substantially prevents coring of the surgical wall as the suture passer is passed through the surgical wall during a wound repair procedure.

In certain embodiments, the jaw is sized such that a sufficient clearance remains between an edge of the jaw and an inner surface of the elongate tube to allow a suture to lie securely between the inner surface of the elongate tube and the edge of the jaw without being torn as the suture passer is passed through the surgical wall.

In some examples, the grasping member is manufactured as a single component (e.g., by stamping the arms and the base from a single piece of metal). This can reduce the likelihood of an arm breaking off from the grasping member and thereby falling into the surgical cavity as the suture passer is being passed through the surgical wall or while the distal end of the suture passer is disposed within the surgical cavity.

In certain embodiments, surgical procedures utilizing the suture passer can be performed without coring the surgical wall. Using the suture passer to repair a wound while preventing tissue coring can accordingly eliminate trauma to the surgical wall that would be associated with the tissue coring, prevent infection that may result from a section of cored tissue being pushed into the surgical cavity as a suture passer is passed through the surgical wall, and further prevent the section of cored tissue from becoming lodged within the elongate tube.

In addition, wound repair procedures utilizing the suture passer described herein can allow the suture passer to be passed through a surgical wall with less force as compared to otherwise similar suture passers having open elongate tubes. Elimination of the coring action that would otherwise be performed by the elongate tube reduces the total amount of force required to pass the suture passer through the surgical wall. Reduction of the force required to pass the suture passer through the surgical wall further reduces the probability that the suture will tear as the suture is sandwiched between a section of the surgical wall and the suture passer while the suture passer is being passed through the surgical wall.

Other aspects, features, and advantages will be apparent from the description and drawings, and from the claims.

DETAILED DESCRIPTION

Figure 1:
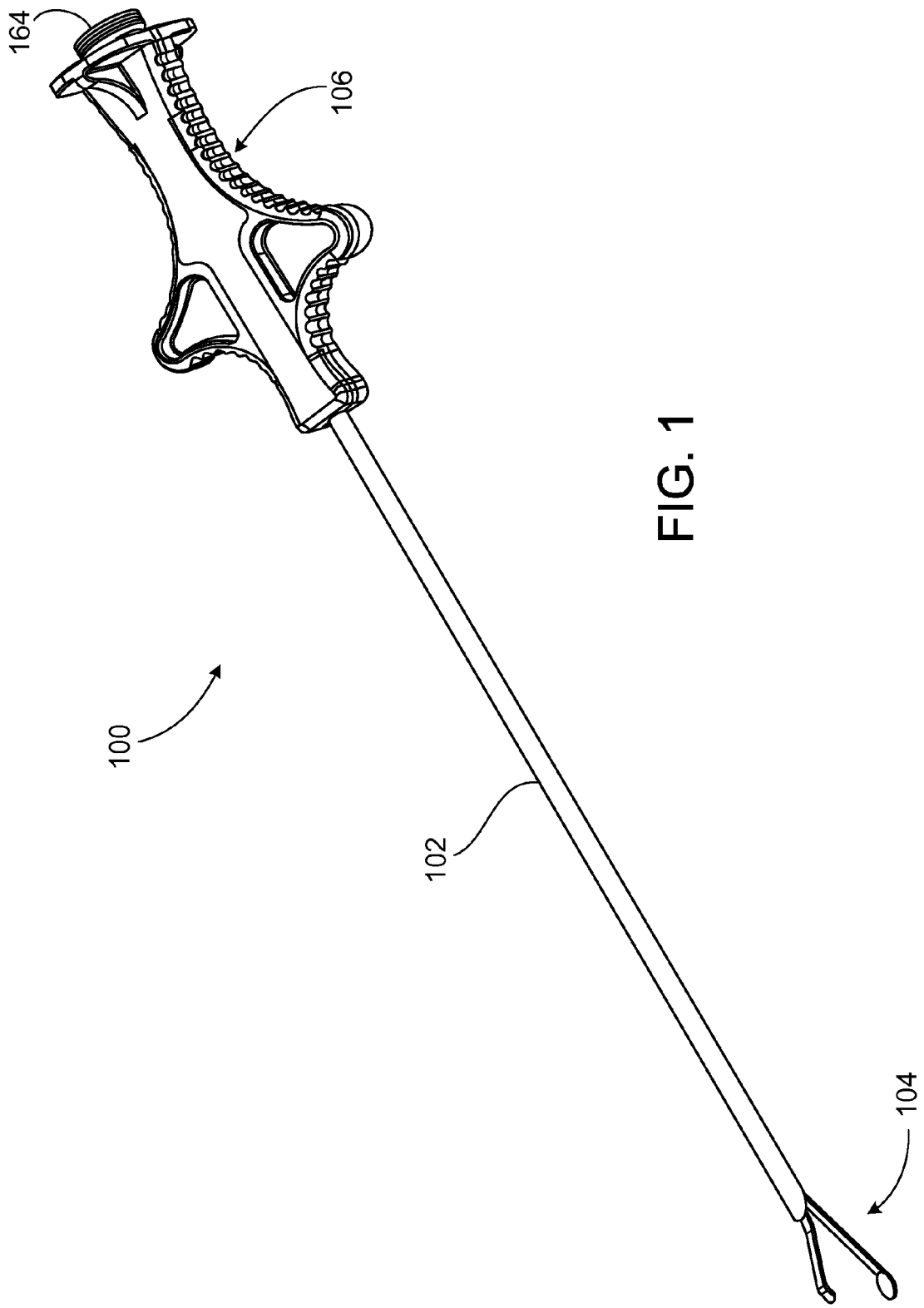
FIG. 1 is a perspective view of suture passer including a handle and an extendable grasping member surrounded by an elongate tube.

FIG. 1 illustrates a suture passer 100 that includes an elongate tube 102, a grasping member 104, and a handle 106. The elongate tube 102 is formed to pierce tissue such that the suture passer 100 can be passed through a surgical wall (e.g., an abdominal wall) and into a surgical cavity (e.g., a peritoneal cavity). The grasping member 104 can be extended from a distal end of the elongate tube 102 and is configured to grasp a suture for delivery of the suture into the surgical cavity or retrieval of the suture from the surgical cavity. During use, a user can grasp the handle 106 and depress/release a button 164 extending from the proximal end of the handle 106 in order to extend/retract the grasping member 104.

Figure 2:
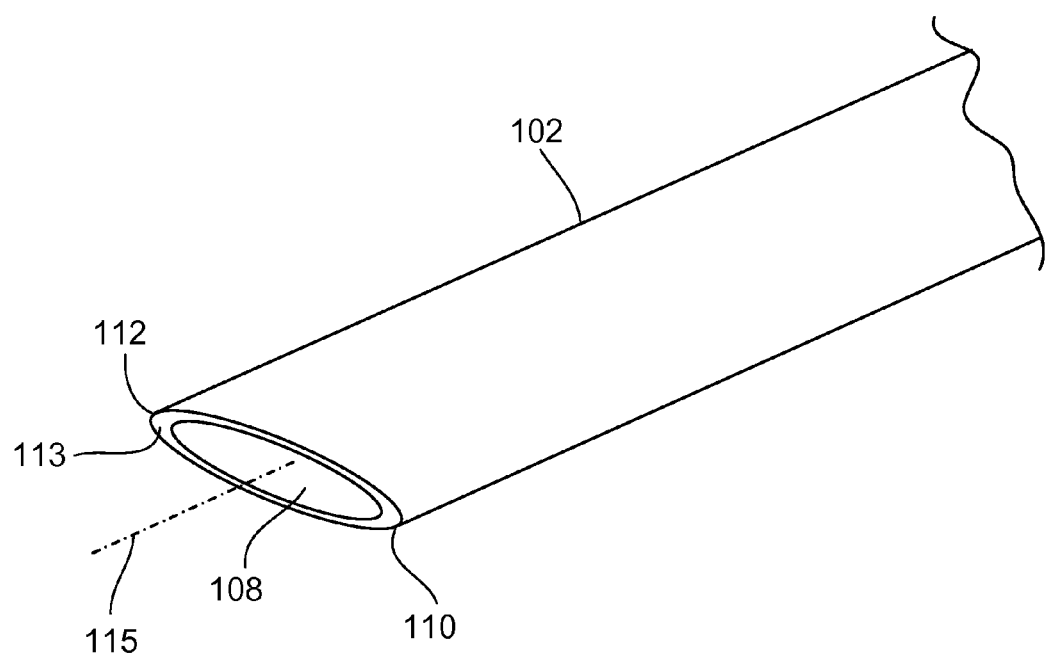
FIG. 2 is a perspective view of a distal end region of the elongate tube of the suture passer FIG. 1.

Referring to FIG. 2, the elongate tube 102 defines a central lumen and includes a beveled distal end region that forms a distal opening 108. The opening 108 is defined in part by a proximal edge 110 and a distal edge 112 of the beveled distal end region. The proximal and distal edges 110, 112 are sufficiently sharp such that they can pierce a surgical wall to allow the suture passer 100 to be passed through the surgical wall and into the surgical cavity. An annular end surface 113 of the elongate tube 102 typically forms an acute angle of about 15° to about 30° (e.g., about 30°) with a longitudinal axis 115 of the elongate tube 102. The beveled configuration of the distal end region of the elongate tube 102 helps to ensure that the suture passer 100 can be passed through a surgical wall with relative ease (i.e., by applying relatively little force to the suture passer 100). The opening 108 of the elongate tube 102 typically has a diameter of about 0.050 inch to about 0.110 inch (e.g., about 0.092 inch), and the elongate tube 102 typically has an outer diameter of about 0.060 inch to about 0.125 inch (e.g., about 0.108 inch). While the grasping member 104 (shown in FIG. 1) is retracted within the elongate tube 102 and as the suture passer 100 contacts the surgical wall, the distal edge 112 pierces the surgical wall and thus allows entry of the suture passer 100 into the surgical wall. Absent the grasping member 104, the proximal edge 110 of the elongate tube 102 could potentially core (i.e., cut out a mass of tissue) the surgical wall as the suture passer 100 is passed through the surgical wall. By plugging the opening 108 of the elongate tube 102 with the grasping member 104 in the manner described below, the tendency to core the surgical wall can be reduced.

Figure 3:
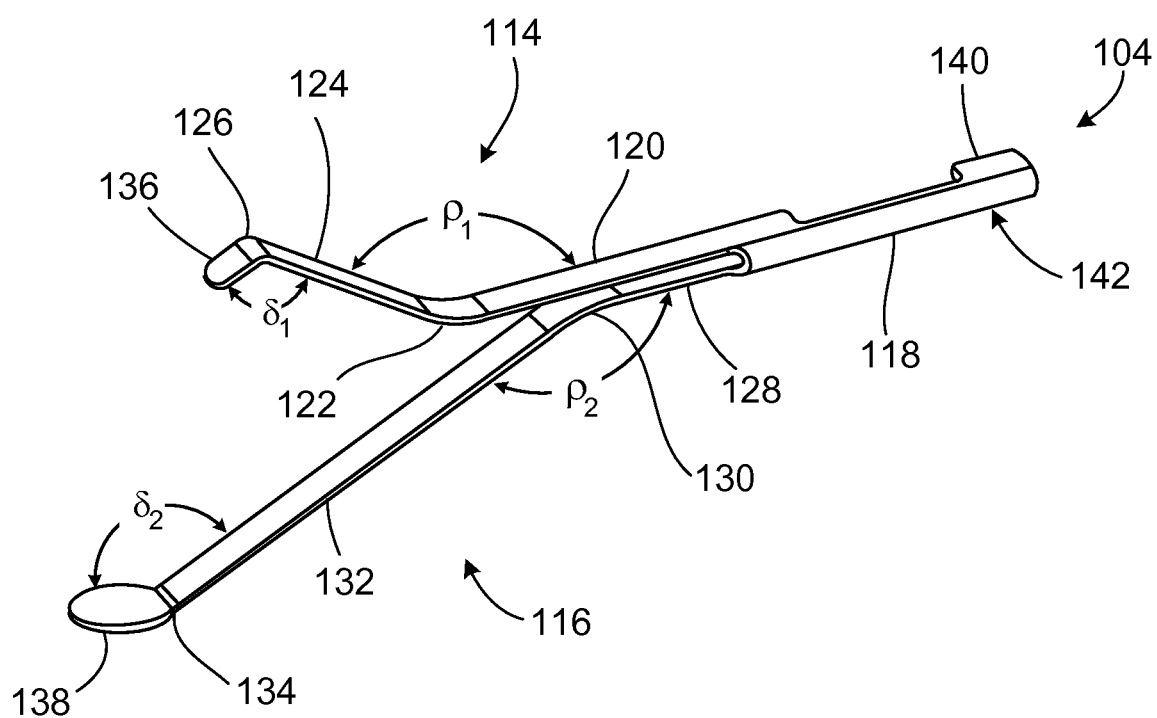
FIG. 3 is a perspective view of the grasping member of the suture passer of FIG. 1.

Referring to FIG. 3, the grasping member 104 includes spaced apart first and second arms 114, 116 that extend from a common base 118 that has a u-shaped cross-sectional shape. The first arm 114 is shorter than the second arm 116. The first arm 114 includes a first proximal section 120, a first proximal bend 122, a first distal section 124, and a first distal bend 126 from which a first jaw 136 extends. Similarly, the second arm 116 includes a second proximal section 128, a second proximal bend 130, a second distal section 132, and a second distal bend 134 from which a second jaw 138 extends. An extension length of the first arm 114 (i.e., a length of the first distal section 124 plus a length of the first jaw 136) is shorter than an extension length of the second arm 116 (i.e., a length of the second distal section 132 plus a length of the second jaw 138). The extension length of the first arm 114 can, for example, be about 0.060 inch to about 0.150 inch (e.g., about 0.100 inch) shorter than the extension length of the second arm 116. The first arm 114 typically has an extension length of about 0.700 inch to about 1.0 inch, while the second arm 116 typically has an extension length of about 0.75 inch to about 1.25 inches. The first proximal bend 122 is distally spaced from the second proximal bend 130, and the bend radii of the first and second proximal bends 122, 130 differ from one another. The offset between the first and second proximal bends 122, 130 causes the first arm 114 to be snapped towards the second arm 116 as the grasping member 104 is retracted within the elongate tube 102, thereby causing the first jaw 136 to snap against the second jaw 138. This action allows a suture to be secured or trapped between the two jaws 136, 138. The offset between the first and second proximal bends 122, 130 is typically about 0.060 inch to about 0.130 inch. The first proximal bend radius is smaller than the second proximal bend radius, thus defining a first proximal angle $\rho_1$ that is less than a second proximal angle $\rho_2$, where $\rho_1$ and $\rho_2$ are measured from the first and second proximal sections 120, 128 to the first and second distal sections 124, 132, respectively. The first and second proximal bend radii are typically about 0.050 inch to about 0.150 inch and about 0.050 inch to about 0.150 inch, respectively. Accordingly, the angle $\rho_1$ is typically about 130° to about 150°, while the angle $\rho_2$ is typically about 130° to about 160°.

The first distal bend 126 is proximally spaced from the second distal bend 134, and the bend radii of the first and second distal bends 126, 134 differ from one another. The offset between the first and second distal bends 126, 134 causes a distal end of the first jaw 136 to contact a center region of the second jaw 138 as the grasping member 104 is retracted within the elongate tube 102 and the first arm 114 accordingly snaps towards the second arm 116. The offset between the first and second distal bends 122, 130 is typically about 0.05 inch to about 0.125 inch. The first distal bend radius is smaller than the second distal bend radius, thus defining a first distal angle $\delta_1$ that is less than a second distal angle $\delta_2$, where $\delta_1$ and $\delta_2$ are measured from the first and second distal sections 126, 134 to the first and second jaws 136, 138, respectively. The first and second distal bend radii are each typically about 0.050 inch to about 0.125 inch. The angle $\delta_1$ is typically about 100° to about 150°, while the angle $\delta_2$ is typically about 130° to about 160°.

The second jaw 138 is sufficiently sized and shaped such that the jaw 138 can substantially cover the opening 108 of the elongate tube 102 while the grasping member 104 is retracted within the elongate tube 102. As shown in FIG. 3, the second jaw 138 has an elliptical shape that approximately matches the shape of the opening 108 in the beveled distal end of the elongate tube 102 (shown in FIGS. 1 and 2). In some embodiments, the second jaw 138 covers about 80% to about 95% of an area of the opening 108. The second jaw 138 is sized such that a sufficient clearance remains between an edge of the second jaw 138 and an inner surface of the elongate tube 102 to allow a suture to lie securely between the inner surface of the elongate tube 102 and the edge of the second jaw 138 without being torn as the suture passer 100 is passed through the surgical wall. The clearance between the edge of the second jaw 138 and the inner surface of the elongate tube 102 is typically about 0.005 inch to about 0.02 inch to allow for the carrying of standard sutures.

Still referring to FIG. 3, the base 118 of the grasping member 104 extends from proximal ends of the arms 114, 116 and includes first and second flanges 140, 142 extending parallel to the arms 114, 116, respectively. The base 118 of the grasping member typically has a length of about 0.2 inch to about 7 inches. A total length of the grasping member 104 (i.e., the length of the base 118 plus the length of the second arm 116 as measured along a central axis of the grasping member 104) is typically about 1.25 inches to about 8.5 inches.

Figure 4:
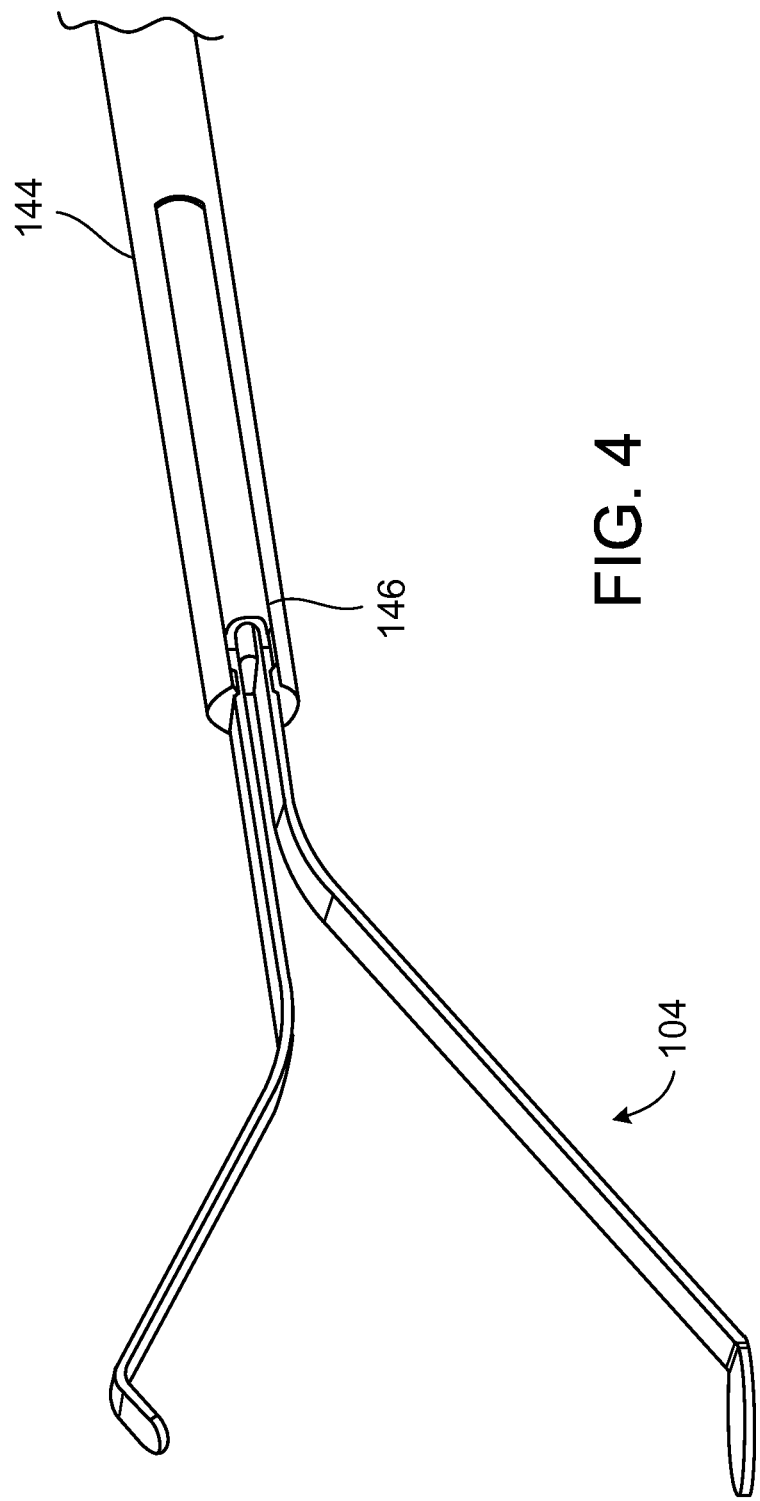
FIG. 4 is a perspective view of the grasping member of FIG. 3 coupled to an internal rod that is positioned within a lumen of the elongate tube of the suture passer of FIG. 1 when the suture passer is assembled.
Figure 5:
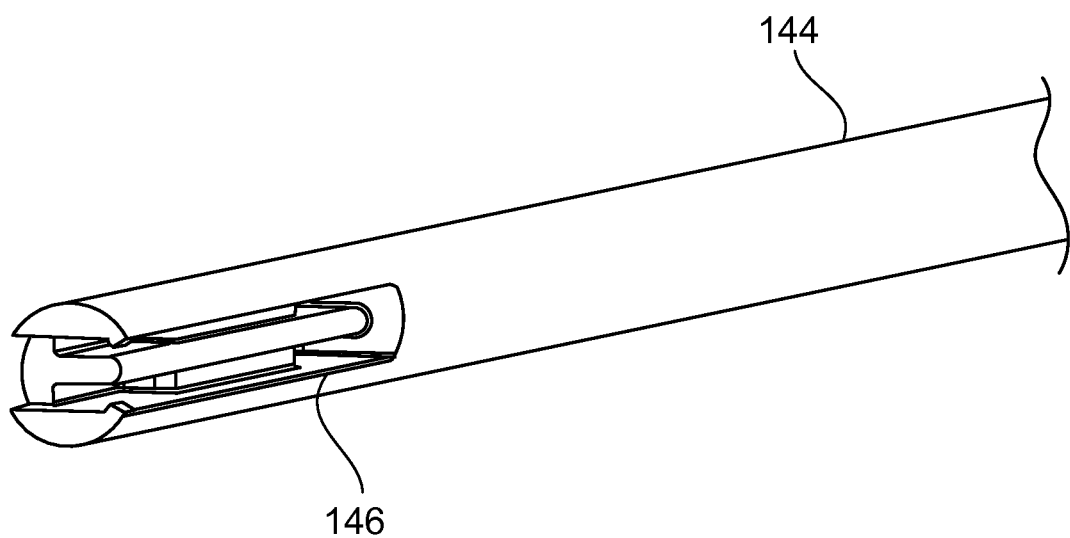
FIG. 5 is a perspective view of a distal end region of the internal rod of FIG. 4.

Referring to FIGS. 4 and 5, the base 118 of the grasping member 104 is formed to engage a distal end region of an internal rod 144 disposed within the elongate tube 102 (shown in FIGS. 1 and 2). The distal end region of the internal rod 144 includes a seat 146 formed complimentary to the base 118, such that the base 118 can be securely snapped into the seat 146. In particular, the seat 146 defines a slot having distal projections. The u-shaped base 118 slides into the slot and is retained by the projections. A proximal end region of the internal rod 144 is coupled to the button 164 of a plunger assembly housed within the handle 106. Axial movement of the internal rod 144, which can be caused by depressing and releasing the button 144, causes the grasping member 104 to extend and retract.

Figure 6:
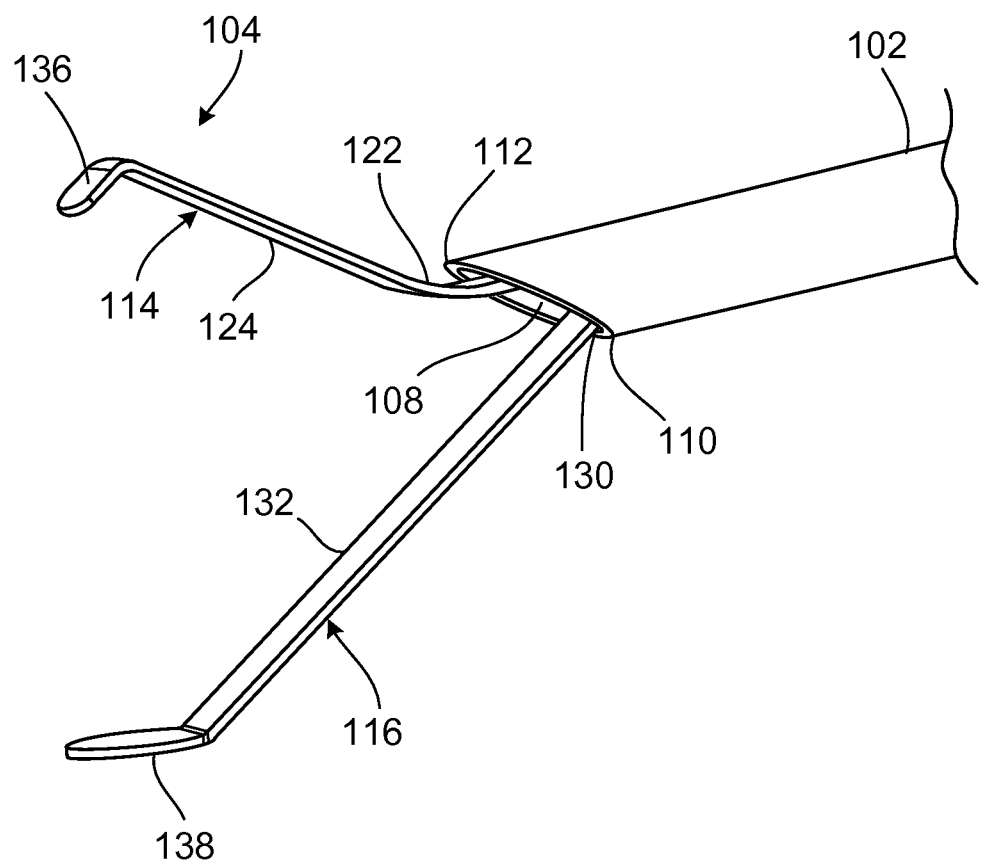
FIG. 6 is a perspective view of a distal end region of the suture passer of FIG. 1 with the grasping member in an extended configuration.

FIG. 6 shows the grasping member 104 extended distally from the opening 108 of the elongate tube 102. When the grasping member 104 is fully extended from the opening 108, the first proximal bend 122 of the first arm 114 is distally spaced from the distal edge 112 of the elongate tube 102. In some examples, the first proximal bend 122 is distally spaced about 0.125 inch from the distal edge 112. The second proximal bend 130 of the second arm 116 is substantially aligned with the proximal edge 110 of the elongate tube 102. In this extended configuration, the first and second arms 114, 116 and jaws 136, 138 are laterally spaced from one another a sufficient distance to allow a suture to be received between the arms 114, 116.

Figure 7:
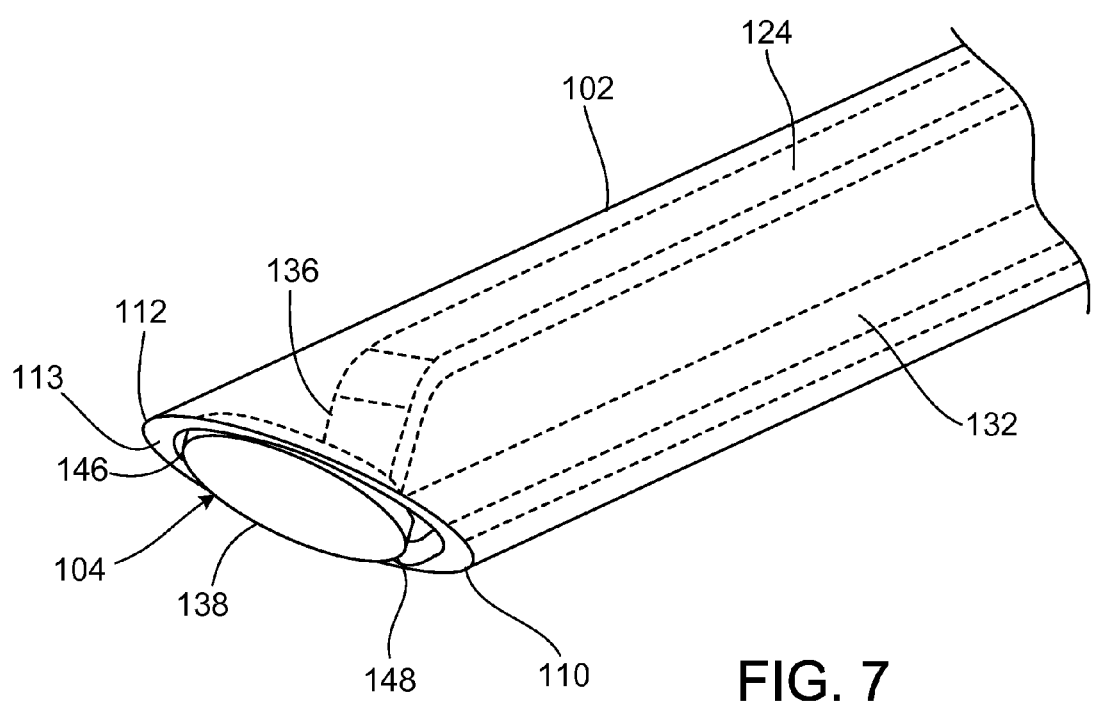
FIG. 7 is a perspective view of the distal end region of the suture passer of FIG. 1 with the grasping member in a retracted configuration.

FIG. 7 shows the grasping member 104 retracted within the central lumen of the elongate tube 102. As the grasping member 104 is retracted within the elongate tube 102 from an extended configuration, the distal edge 112 of the elongate tube 102 encounters the first proximal bend 122 of the first arm 114 and snaps the first arm 114 and first jaw 136 inward. Similarly, the second distal section 132 of the second arm 116 moves along the proximal edge 110 and is deflected inward. As this occurs, the snapping action of the first arm 114 causes the first jaw 136 to snap against the second jaw 138. When the grasping member is fully retracted within the central lumen of the elongate tube 102, a first edge 146 of the second jaw 138 is aligned substantially flush with the distal edge 112 of the elongate tube 102, while a second edge 148 of the second jaw 138 protrudes slightly distally from the proximal edge 110 of the beveled distal end region of the elongate tube 102. In some embodiments, the second edge 148 of the second jaw 138 protrudes about 0 inch (i.e., in an embodiment where the second edge 148 of the jaw 138 is substantially flush with the proximal edge 110 of the elongate tube 102) to about 0.050 inch from the proximal edge 110 of the elongate tube 102. The slight protrusion of the second edge 148 prevents the proximal edge 110 of the elongate tube 102 from piercing the surgical wall as the suture passer 100 is passed through the surgical wall and thus substantially prevents coring (i.e., cutting out a mass of tissue) of the surgical wall.

Figure 8:
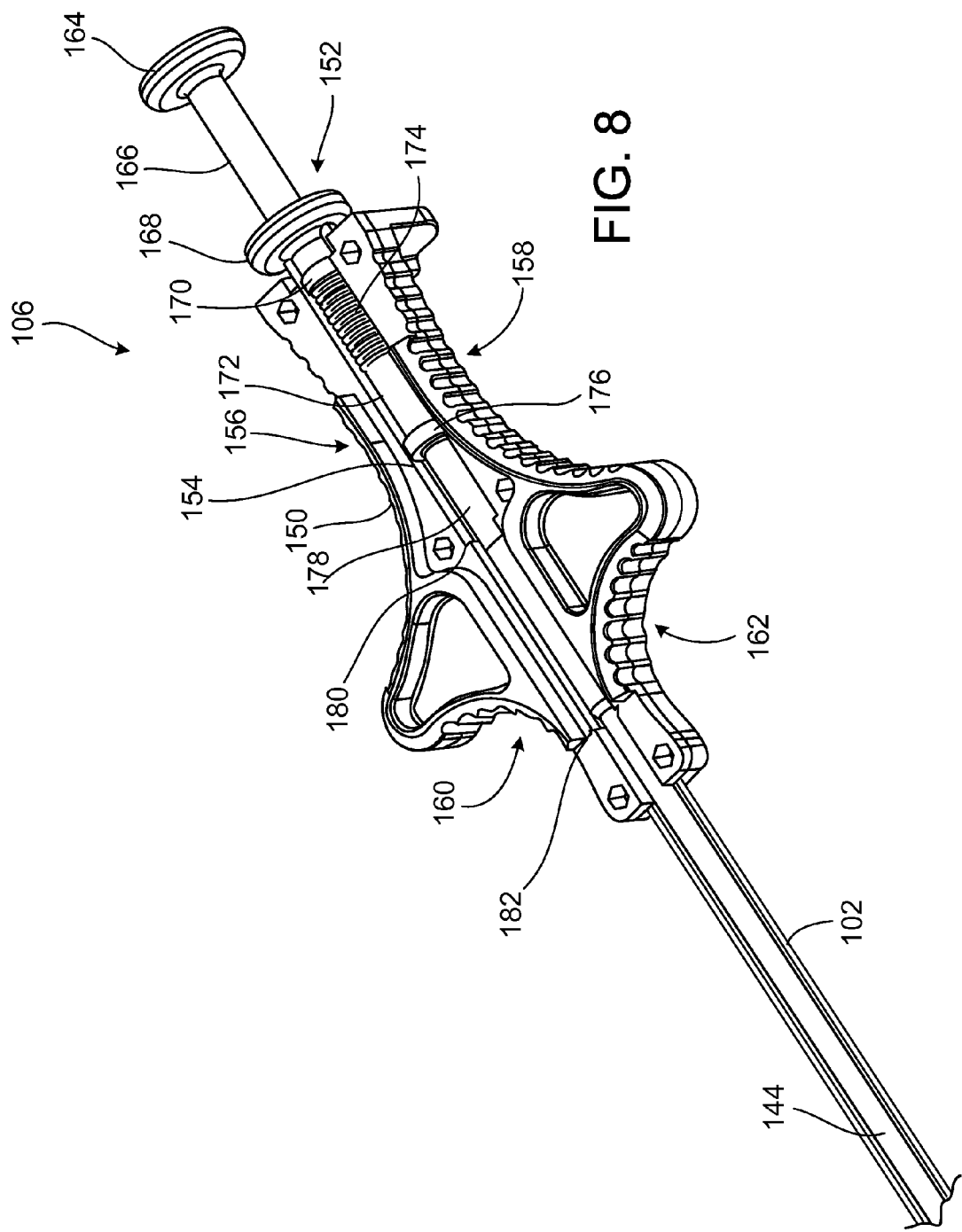
FIG. 8 is a perspective view of the handle of the suture passer of FIG. 1.

Referring now to FIG. 8, the handle 106 includes an outer housing 150 (shown with a top portion cut away) and a plunger assembly 152 seated partially within an internal channel 154 formed by the outer housing 150. The outer housing 150 includes four sets of ridges 156, 158, 160, 162 that provide finger grip surfaces for the suture passer 100. The plunger assembly 152 includes the button 164, a plunging tube 166 extending from the button 164, and a button stop 168 surrounding the plunging tube 166 and disposed adjacent a proximal end of the outer housing 150. The plunger assembly 152 further includes a proximal lip 170 coupled to a distal end of the plunging tube 166, a proximal inner tube 172 having an outer diameter allowing the proximal inner tube 172 to slide longitudinally within the plunging tube 166, a spring 174 surrounding the proximal inner tube 166, and a distal lip 176 coupled to a distal end of the proximal inner tube 166. The plunger assembly 144 further includes a distal inner tube 178 coupled at its proximal end to the distal lip 176 of the proximal inner tube 166 and coupled at its distal end to a proximal end region of the internal rod 144. The elongate tube 102 (shown in FIG. 8 with a top portion cut away) extends distally from the housing 150 and houses the internal rod 144.

In FIG. 8, the plunger assembly 152 is shown proximally retracted, such that the spring 174 is in a resting, uncompressed state and is disposed near a proximal end of the outer housing 150. Accordingly, the proximal inner tube 172, the distal inner tube 178, and the internal rod 144 are positioned sufficiently proximal such that the grasping member 104 is disposed substantially within the central lumen of the elongate tube 102, as illustrated in FIG. 7. Conversely, when the grasping member 104 is extended from the opening 108 of the elongate tube 102, the spring 174 is compressed against the distal lip 176 by the proximal lip 170 of the proximal inner tube 172, causing the spring 174 to move distally within the internal channel 154 until the distal lip 176 rests against a proximal channel stop 180. Accordingly, the internal rod 144 is shifted distally within the internal channel 154 until it rests against a distal channel stop 182, which exposes the grasping member 104 at the beveled distal end region of the elongate tube 102, as illustrated in FIG. 6. In some examples, the distance by which the plunging tube 166 can be shifted distally is about 0.5 inch to about 1.5 inches (e.g., 0.75 inch), such that the internal rod 144 and the grasping member 104 are likewise shifted distally by about 0.5 inch to about 1.5 inches (e.g., about 0.75 inch) when the grasping member 104 is fully extended from the opening 108 of the elongate tube 102.

In some embodiments, a total length of the suture passer 100 (as measured from the distal edge 112 of the elongate tube 102 to the button stop 168) is about 9 inches to about 11 inches. However, the suture passer 100 can have any of various different dimensions depending on the application for which it is to be used.

The various components of the suture passer 100, including the elongate tube 102, the grasping member 104, the handle 106, the internal rod 134, and the plunger assembly 144 can be formed of one or more of a variety medical grade materials, including stainless steel, titanium, polycarbonate, Acrylonitrile butadiene styrene (ABS), polypropylene, acrylic, liquid crystal polymer (LCP), polyetheretherketone (PEEK), silicone, and thermoplastic elastomer (TPE).

Various different manufacturing techniques can be used to make and assemble the various components of the suture passer 100. In some embodiments, the elongate tube 102 is manufactured via a tube drawing process. In certain embodiments, the grasping member 104 is manufactured via a metal stamping process. Manufacturing the grasping member 104 as one component (e.g., in cases where the arms 114, 116 and the base 118 are stamped from a single piece of metal) can reduce the likelihood of an arm 114, 116 breaking off from the grasping member 104 and thereby falling into the surgical cavity of the patient as the suture passer 100 is being passed through the surgical wall or while the distal end of the suture passer 100 is disposed within the surgical cavity. In some instances, the various components of the suture passer 100 are assembled via a press fit process.

Figure 9A:
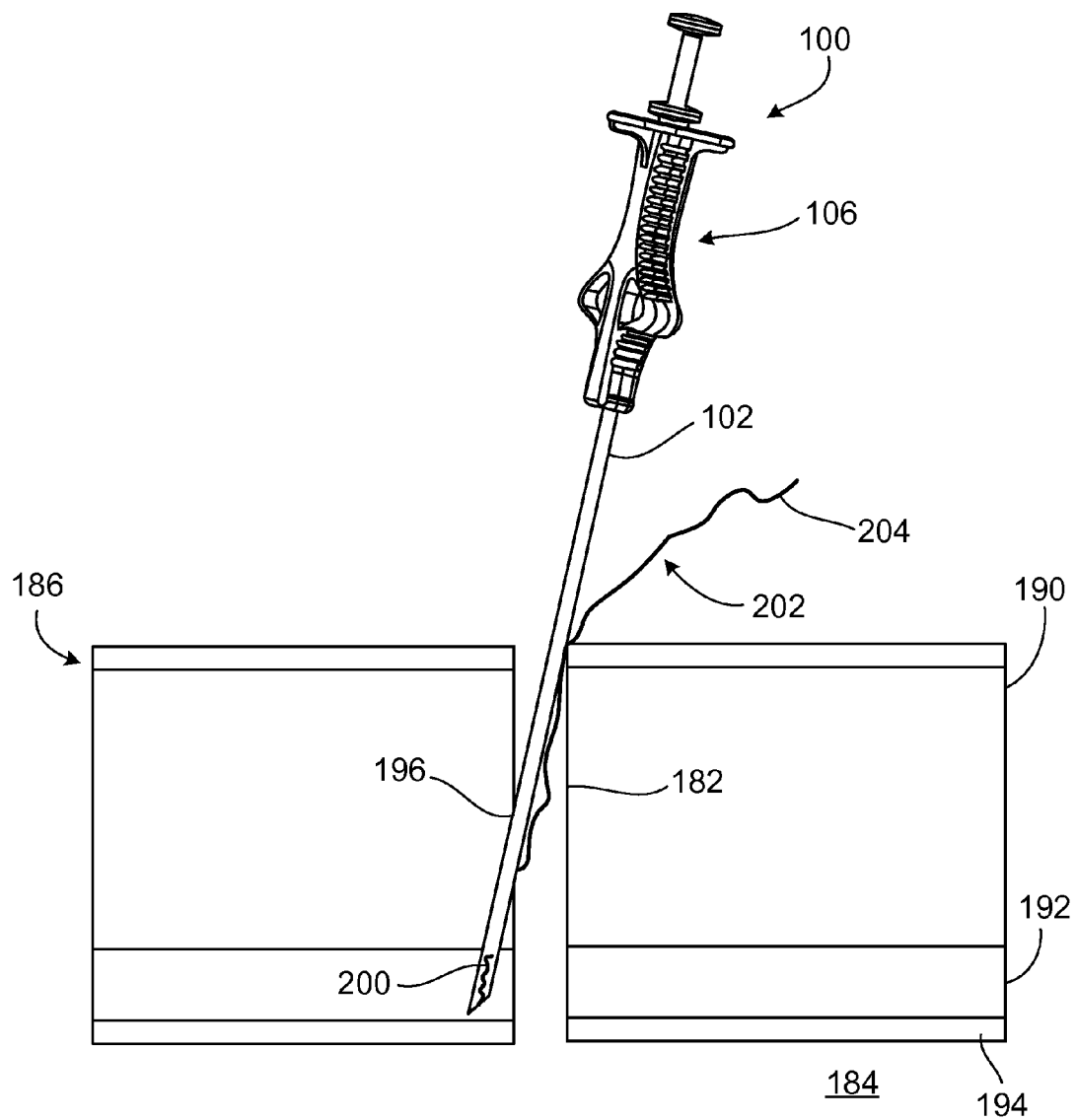
FIGS. 9A-9F schematically illustrate a method of repairing an endoscopic port site wound using the suture passer of FIG. 1.

FIGS. 9A-9F schematically illustrate a method of using the suture passer 100 to repair a port site wound 182 resulting from a laparoscopic surgical procedure in an abdominal cavity 184 of a patient. Using the suture passer 100 to repair the wound 182 can enable closing of the wound 182 without substantially coring an abdominal wall 186 surrounding the wound 186 (as will be discussed in detail below). As shown in FIG. 9A, the suture passer 100 is loaded with a suture 202, and the grasping member 104 is retracted to securely retain the suture 202. The suture passer 100 is then passed through various layers of the abdominal wall 186, including a relatively thick fatty layer 190, a fascia layer 192, and a peritoneum 194, at a left puncture point 196 adjacent the port site wound 182.

Figure 9B:
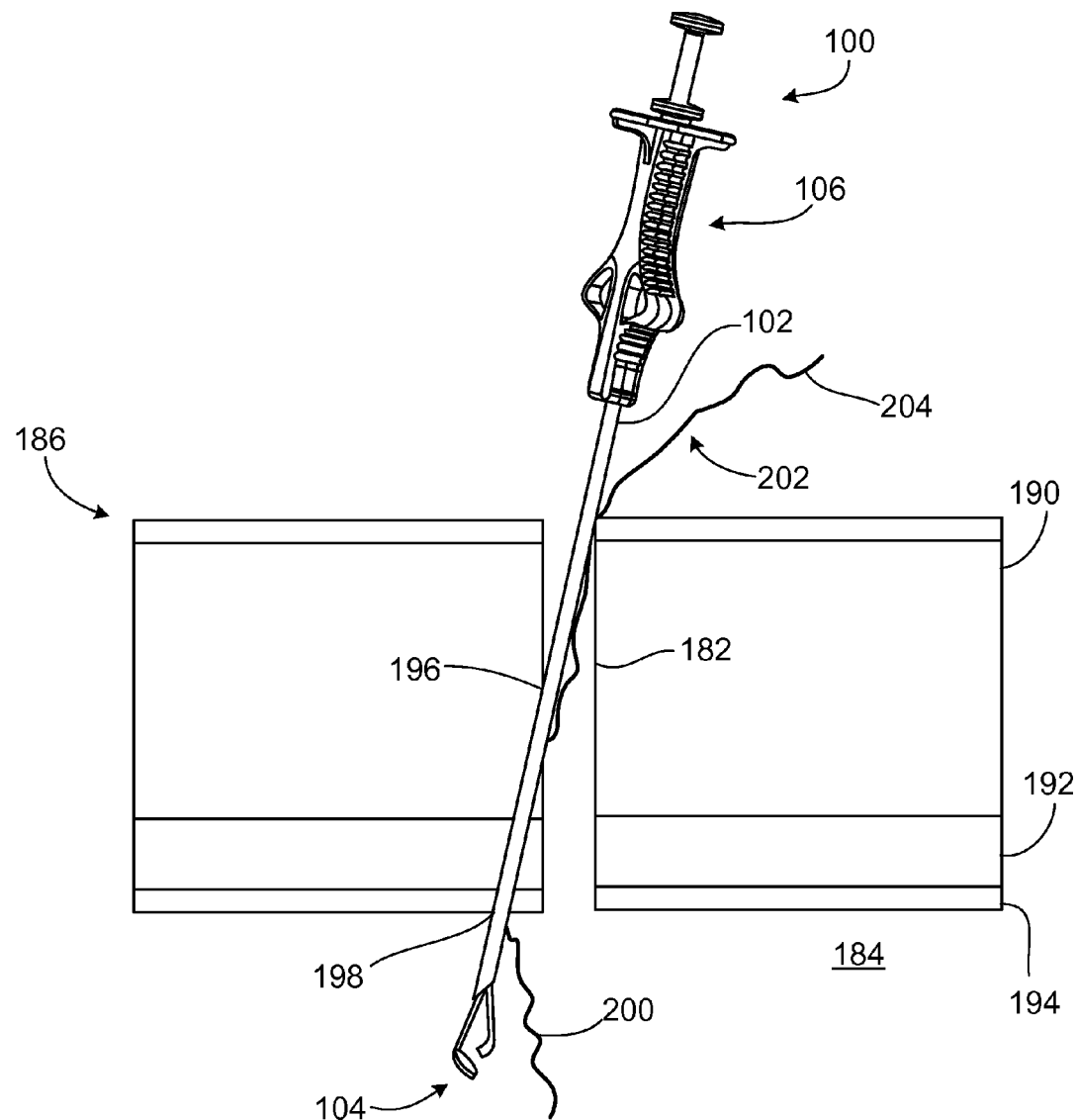

As shown in FIG. 9B, continued advancement of the suture passer 100 causes the suture passer 100 to pass into the abdominal cavity 184 at a left entry point 198 without having substantially cored the abdominal wall 186. The grasping member 104 is then extended from the elongate tube 102 and releases a first end 200 of the suture 202 into the abdominal cavity 184.

Figure 9C:
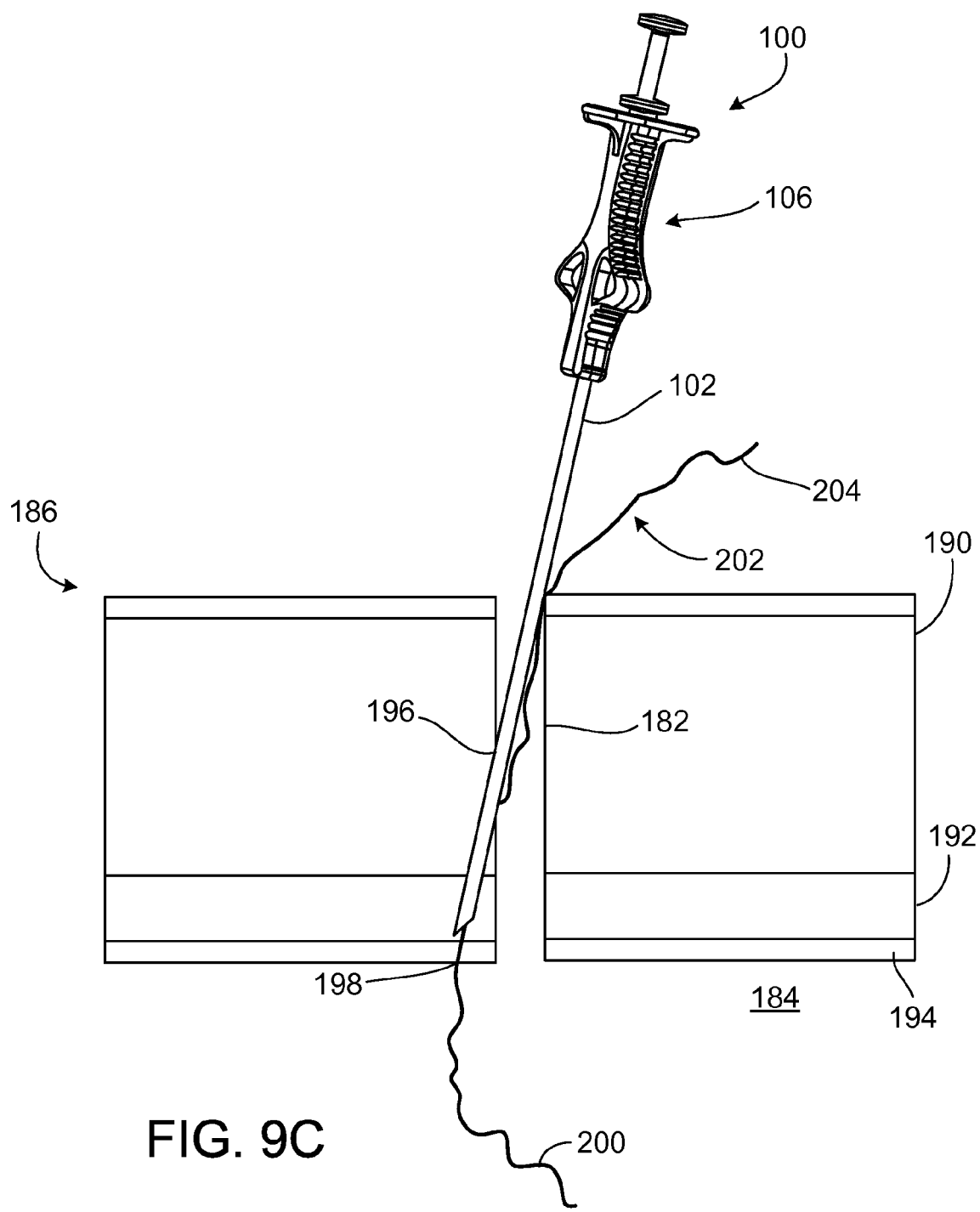

As shown in FIG. 9C, the grasping member 104 is then retracted within the central lumen of the elongate tube 102, and the suture passer 100 is withdrawn from the abdominal wall 186, leaving the first end 200 of the suture 202 in the abdominal cavity 184 while a second end 204 of the suture 202 remains outside of the abdominal wall 186.

Figure 9D:
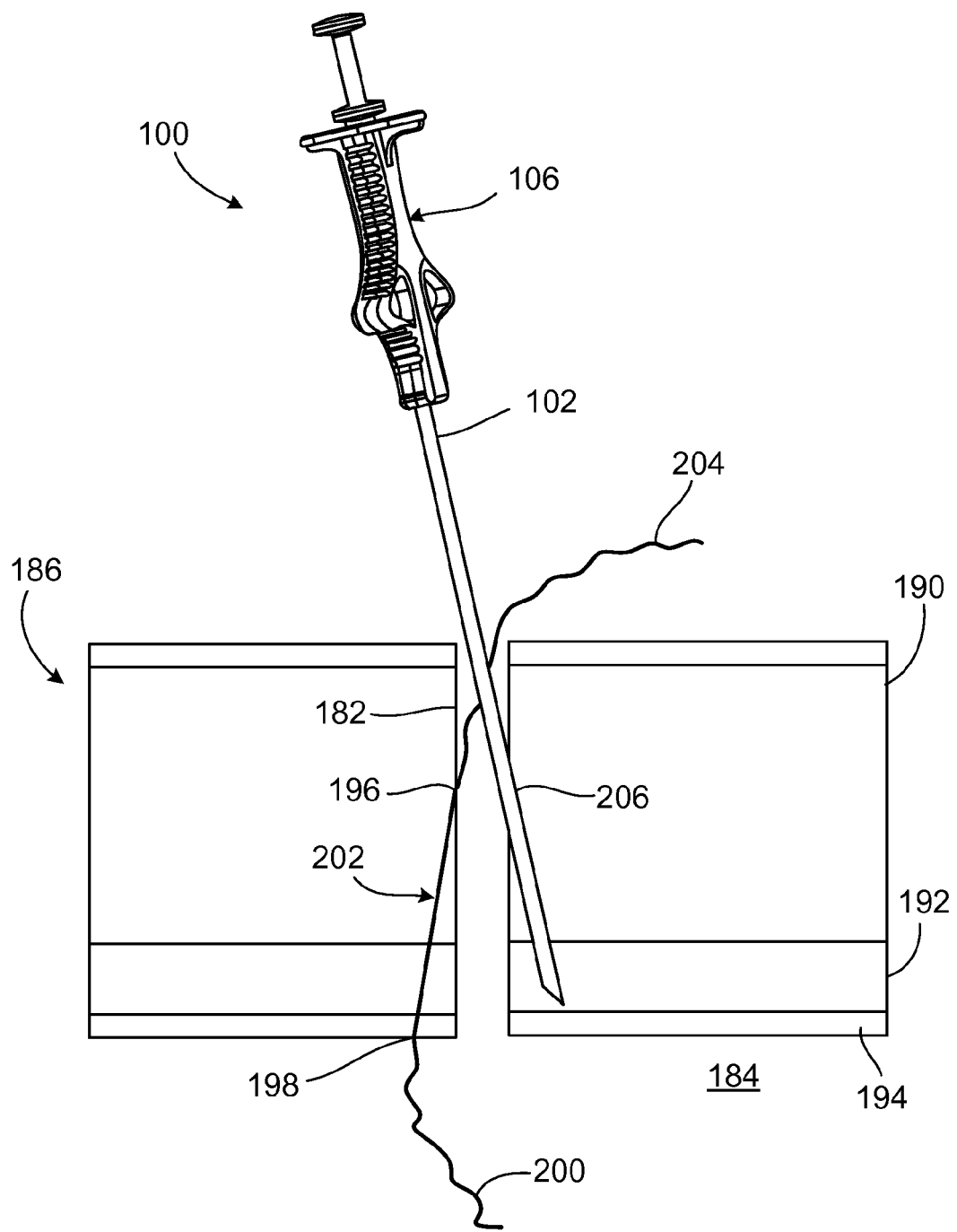

As shown in FIG. 9D, with the grasping member 104 still retracted within the central lumen of the elongate tube 102, the suture passer 100 is subsequently passed through the abdominal wall 186 at a right puncture point 206 adjacent the port site wound 182. The suture passer 100 is passed through the various layers of tissue and into the abdominal cavity 184 in much the same manner described above.

Figure 9E:
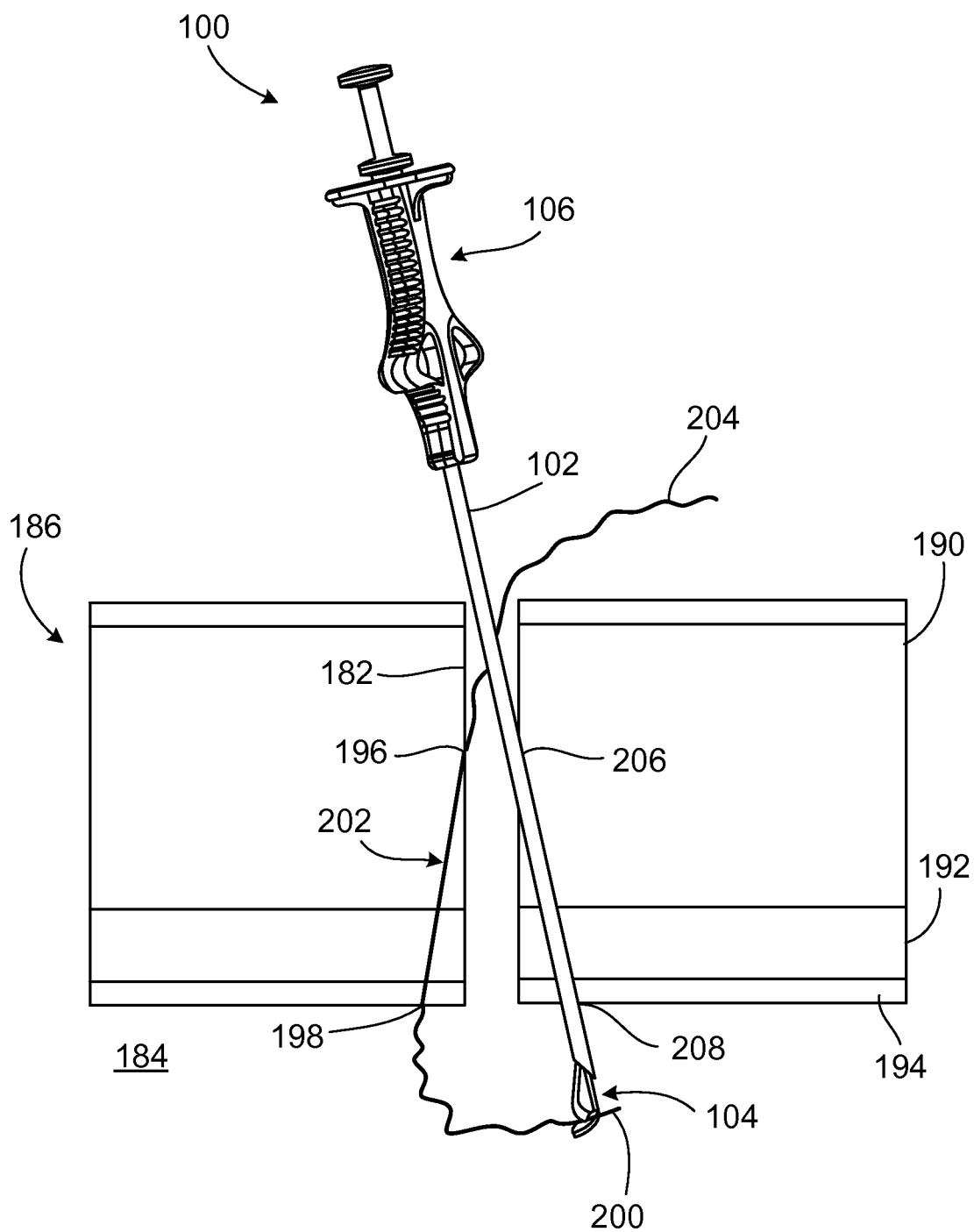

As shown in FIG. 9E, the suture passer 100 passes into the abdominal cavity 184 at a right entry point 208 adjacent the wound 182 (without having substantially cored the abdominal wall 186) and is then shifted to a position where a distal end of the suture passer 100 is in close proximity to the first end 200 of the suture 202, and the grasping member 104 is extended from the elongate tube 102. After positioning the grasping member 104 such that the jaws 136, 138 are on either side of the first end 200 of the suture 202, the grasping member 104 is partially retracted to allow the jaws 136, 138 of the grasping member 104 to grasp the first end 200 of the suture 202. The grasping member 104 is then fully retracted within the central lumen of the elongate tube 102 to draw the suture 202 into the lumen.

Figure 9F:
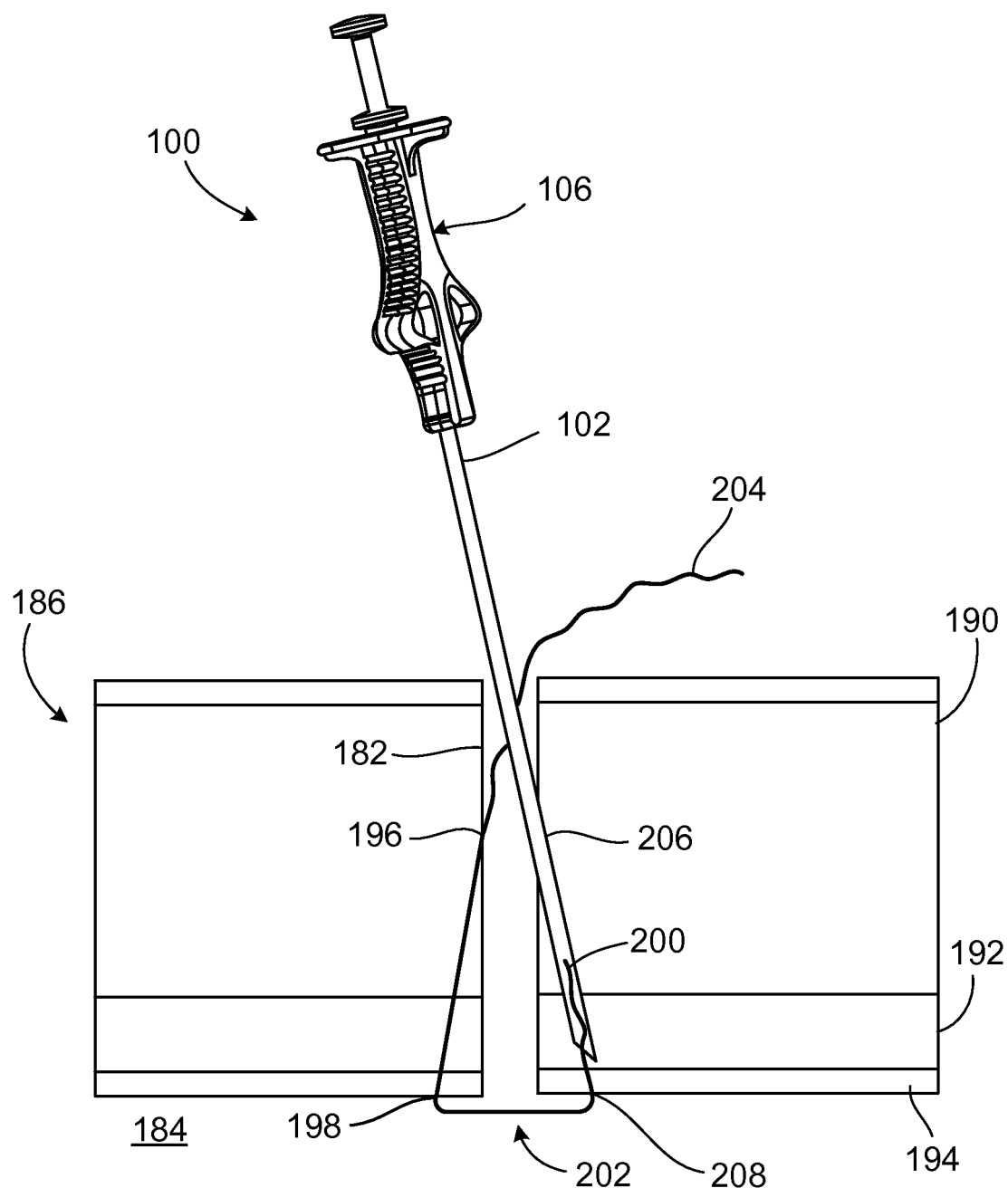

As shown in FIG. 9F, the loaded suture passer 100 is then withdrawn from the abdominal wall 186, pulling the first end 200 of the suture 202 through the right puncture point 206 and outside of the abdominal wall 186.

After removing the suture passer 100 from the abdominal wall 186, the first and second ends 200, 204 of the suture 200 are tied snuggly to form a knot. The knot is positioned at a location proximal to the fascia 192 (i.e., above the fascia 192 in the view shown in FIG. 9F) such that the fascia 192 and peritoneum 194 are substantially closed.

The wound repair procedures described herein can be performed without substantially coring the surgical wall. For example, when the grasping member 104 is retracted within the central lumen of the elongate tube 102, protrusion of the second jaw edge 138 from the proximal edge 110 of the elongate tube 102 substantially prevents the proximal edge 110 of the elongate tube 102 from piercing the surgical wall as the suture passer 100 is being passed through the surgical wall. Accordingly, the suture passer 100 can be passed through the surgical wall without the proximal edge 110 of the elongate tube 102 cutting out a section of tissue that would otherwise extend from a cut formed by the distal edge 112 of the elongate tube 102. Using the suture passer 100 to repair a wound while preventing tissue coring can accordingly eliminate trauma to the surgical wall that would be associated with the tissue coring, prevent infection that may result from a section of cored tissue being pushed into the surgical cavity as a suture passer is passed through the surgical wall, and further avoid jamming of the elongate tube of the suture passer (i.e., lodgment of a cored section of tissue within the elongate tube of the suture passer).

Furthermore, the suture passer 100 can be passed through a surgical wall with less force as compared to otherwise similar suture passers having open elongate tubes. Elimination of the coring action that would result from an open-ended elongate tube reduces the total amount of force required to pass the suture passer 100 through the surgical wall. Reduction of the force required to pass the suture passer 100 through the surgical wall further reduces the probability that the suture will tear as the suture is sandwiched between a section of the surgical wall and the suture passer 100 while the suture passer 100 is being passed through the surgical wall. In conjunction with the reduced force required to pass the suture passer 100 through the surgical wall, the clearance between the edge of the jaw 138 and the internal surface of the elongate tube 102 further prevents tearing of the suture as the suture passer 100 is passed through the surgical wall.

In some instances, the suture passer 100 may be used in conjunction with another device to repair a port site wound. For example, a suture passer guide having one or more guide channels can be placed within the port site wound, and the suture passer 100 can subsequently be passed through the guide channel(s) such that the distal end of the suture passer 100 is accurately guided to a desired entry point into the abdominal cavity. In another example, a suture passer guide including one or more guide channels may be preloaded with a suture and used to deliver a first end of a suture into the abdominal cavity. In such a case, the suture passer 100 can subsequently be passed through the guide channel(s) to retrieve the first and second ends of the suture from the abdominal cavity to continue the wound repair process.

While the elongate tube has been shown as a round tube (i.e., a tube having a circular cross section and an elliptical shaped beveled end region), in some embodiments, the elongate tube may have a different cross-sectional or beveled end shape, such as a square or a rectangle, respectively. In such a case, a jaw may accordingly be sufficiently sized and shaped such that the jaw can substantially cover the opening of the elongate tube while maintaining an appropriate clearance between an edge of the jaw and an inner surface of the elongate tube.

While the grasping member and the internal rod have been described as two separate components, the grasping member and the internal rod can alternatively be formed as a single component that engages the plunger assembly near a distal end region of the suture passer. In some examples, such a single component may be manufactured via a metal stamping process. Other manufacturing techniques, such as die casting and injection molding, can alternatively or additionally be used.

Figure 10:
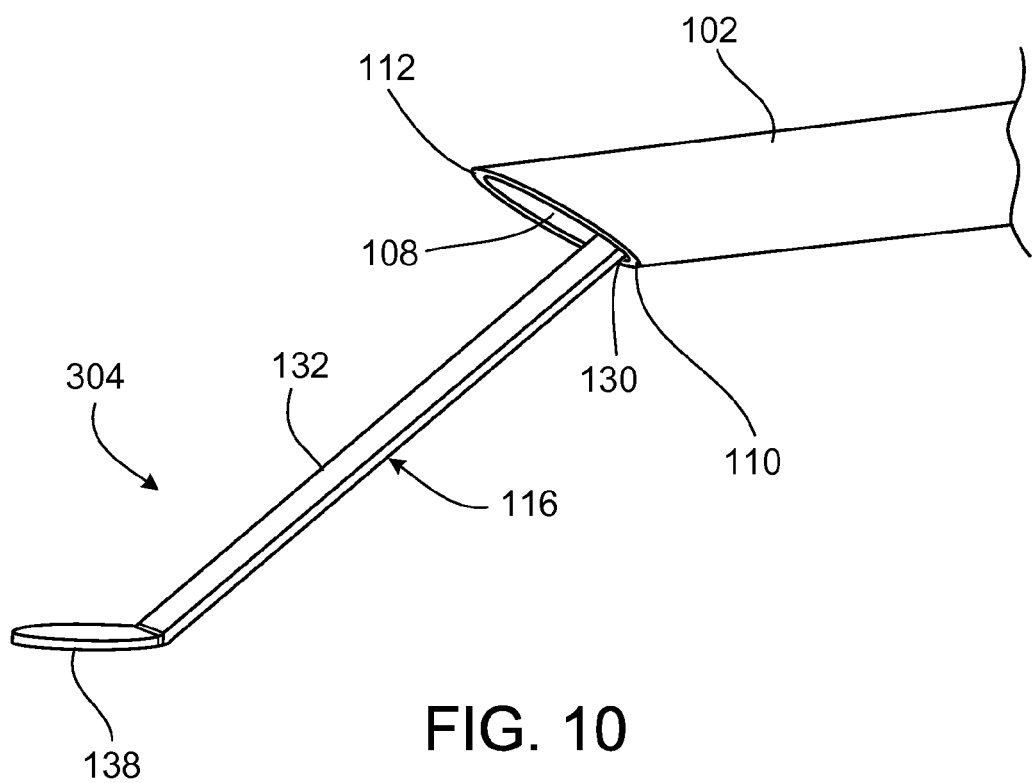
FIG. 10 is a perspective view of a distal end region of a suture passer including a grasping member having only one arm and one respective jaw.
Figure 11:
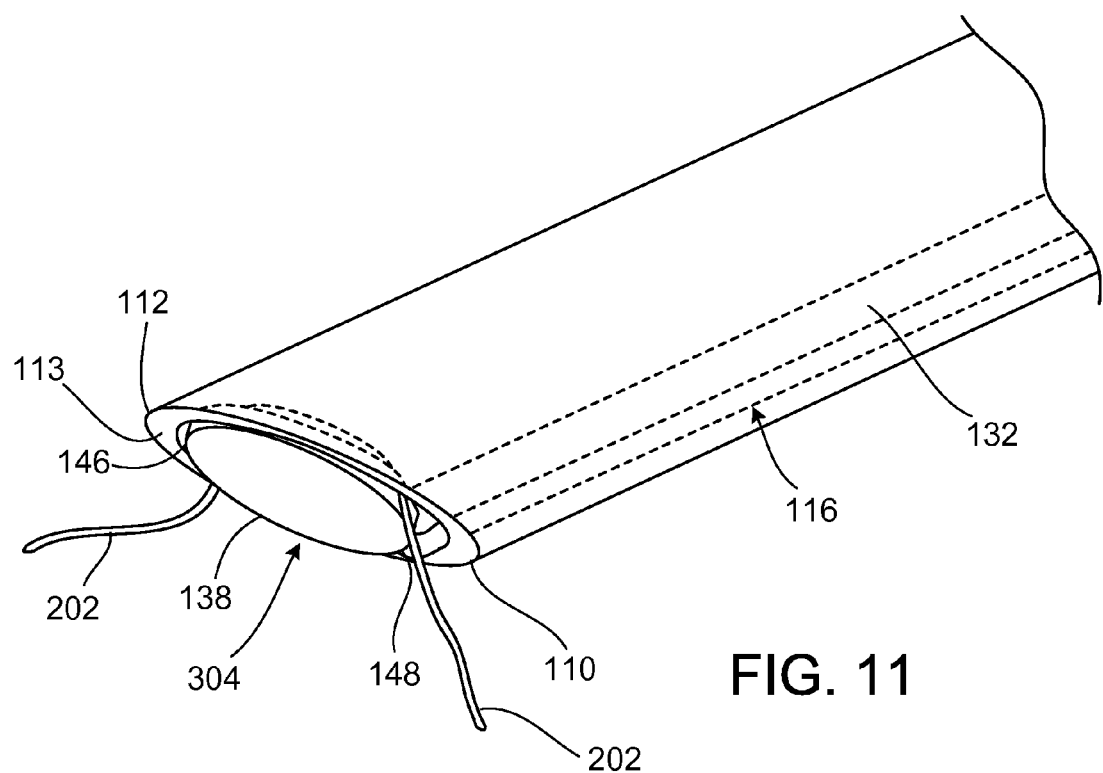
FIG. 11 is a perspective view of the distal end region of the suture passer of FIG. 10 with the grasping member retracted within an elongate tube of the suture passer to secure a suture between the grasping member and the elongate tube.

While the grasping member has been described as including two arms and two jaws, the suture passer can alternatively include a grasping member with a different number of arms and jaws. As shown in FIGS. 10 and 11, for example, a grasping member 304 includes only one arm 116 and one respective jaw 138. The arm 116 and the jaw 138 are substantially similar in construction and function to the arm 116 and the jaw 138 of the grasping member 104. Referring particularly to FIG. 10, the grasping member 304 can be extended from the opening 108 of the elongate tube 102 such that the grasping member 304 can access a suture. Referring to FIG. 11, the grasping member 304 can be retracted such that the suture 202 is hooked around the jaw 138 and secured between the jaw 138 and an internal surface of the elongate tube 102. As shown, the second edge 148 of the jaw 138 protrudes distally from the proximal edge 110 of the beveled end region of the elongate tube 102, which can help to prevent coring of the patient's tissue as the suture passer is passed through the tissue. The remainder of the suture passer can be substantially the same in structure and function to the suture passers described above. For example, the grasping member 304 can further include the base 118, which extends from the proximal end region of the arm 116 and mates with the distal end region of the internal rod 144 included within the suture passer, and the plunger assembly 152 can be used to extend and retract the grasping member 304.

Figures 12, 13:
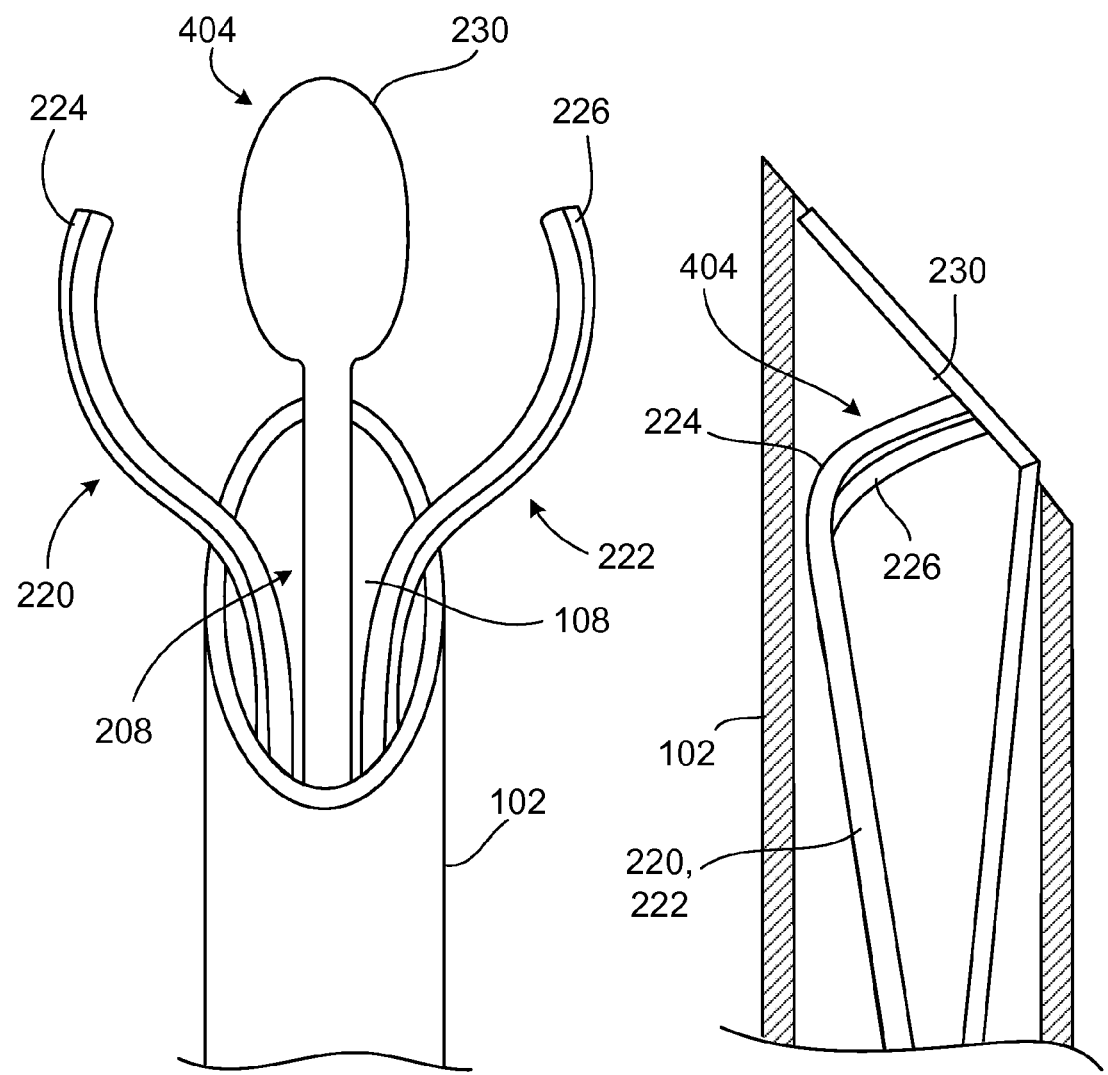
FIG. 12 is a perspective view of a distal end region of a suture passer that includes a grasping member having three arms and three respective jaws, with the grasping member extended from an elongate tube of the suture passer.
FIG. 13 is a cross-sectional side view of the suture passer of FIG. 12 with the grasping member retracted into the elongate tube such that one of the jaws covers a distal opening of the elongate tube.

In certain embodiments, the grasping member includes more than two arms and two respective jaws. As shown in FIGS. 12 and 13, for example, a suture passer includes a grasping member 404 having first and second arms 220, 222 and first and second respective jaws 224, 226. Referring particularly to FIG. 12, the first and second arms 220, 222 and jaws 224, 226 are similar in construction to the arm 114 and the jaw 136. The grasping member 404 further includes a third arm 228 and respective jaw 230 that are similar in construction to the arm 116 and the jaw 138 of the grasping member 104 described above. The grasping member 404 can be extended from the elongate tube 102 and then partially retracted such that the first and second jaws 224, 226 snap shut against a suture and further fully retracted such that the first and second jaws 224, 226 are fully retracted within the elongate tube 102 when the grasping member 404 is fully retracted. The jaw 230 is sufficiently sized and shaped such that it can substantially cover the opening 108 of the elongate tube 102. Furthermore, the jaw 230 is sized such that a sufficient clearance remains between an edge of the jaw 230 and an inner surface of the elongate tube 102 to gently secure a suture therebetween. Referring particularly to FIG. 13, in a retracted configuration, the jaw 230 substantially covers the opening 108 of the elongate tube 102. In addition, as shown in FIG. 13, a proximal edge of the jaw 230 protrudes distally from a proximal edge of the beveled end region of the elongate tube 102, which can help to prevent coring of the patient's tissue as the suture passer is passed through the tissue. The remainder of the suture passer can be substantially the same in structure and function to the suture passers described above. For example, the grasping member 404 can include a common base extending from proximal end regions of arms 220, 224, 228 that is formed to engage with a distal end region of an internal rod included within the suture passer. A proximal end region of the internal rod is coupled to a plunger assembly housed within a handle, which is used to extend and retract the grasping member 404.

Figure 14:
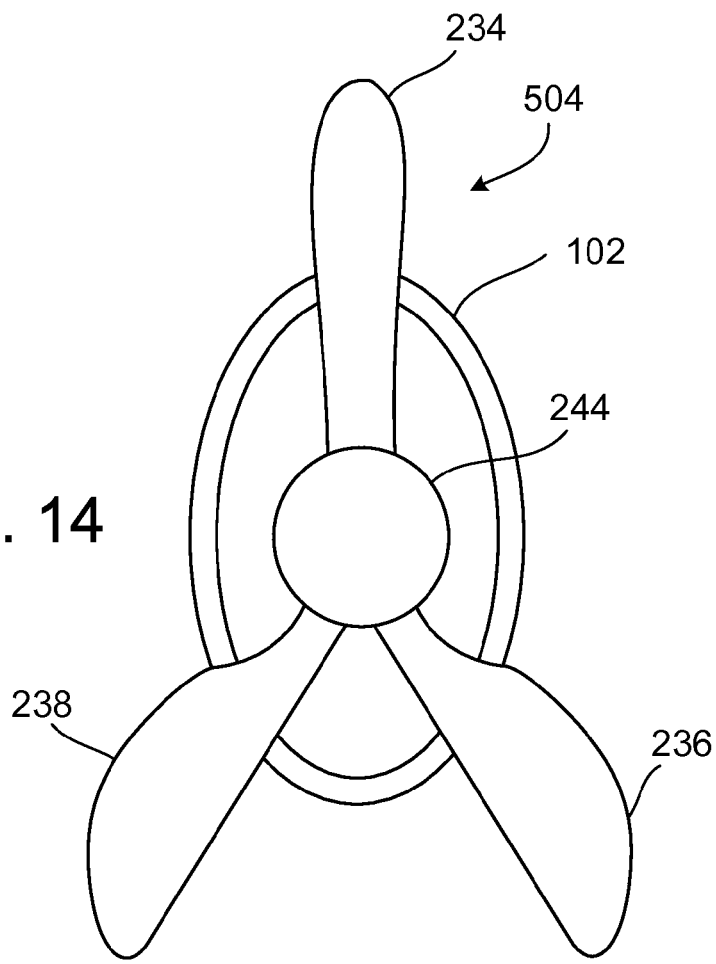
FIG. 14 is a front view of a suture passer including a grasping member having three arms and three respective jaws, with the grasping member extended from an elongate tube of the suture passer.
Figure 15:
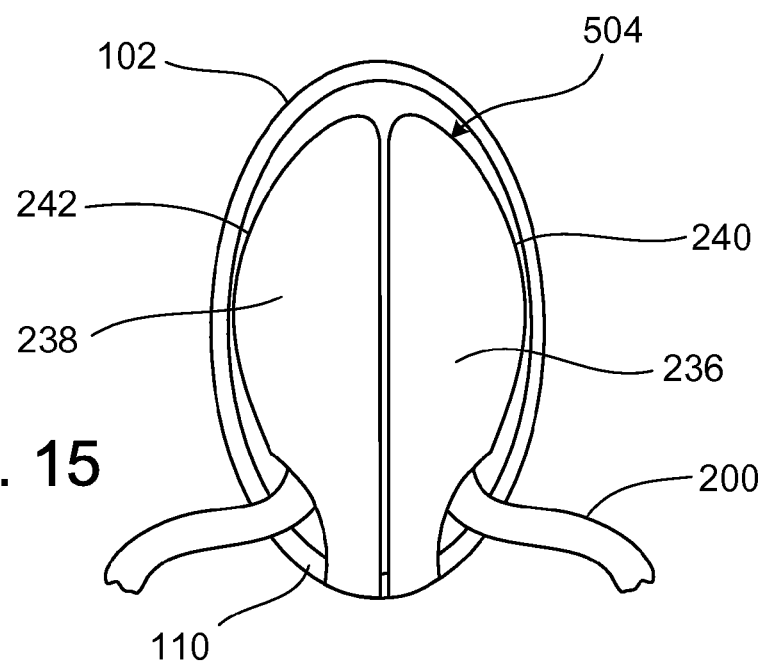
FIG. 15 is a front view of the suture passer of FIG. 14 with the grasping member retracted into the elongate tube such that two of the jaws cover a distal opening of the elongate tube.

In some embodiments, the grasping member is configured so that more than one jaw covers the opening of the elongate tube when the grasping member is retracted within a central lumen of the elongate tube. Referring to FIG. 14, for example, a suture passer includes a grasping member 504 having three jaws 234, 236, 238 that extend from three respective arms. The grasping member 504 can be extended from the elongate tube 102 and then partially retracted such that the three jaws 234, 236, 238 snap shut against the suture 202. Referring to FIG. 15, the grasping member 504 can then be further fully retracted such that the first jaw 234 is fully retracted within the central lumen of the elongate tube 102. The jaws 236, 238 are sufficiently sized and shaped such that when the jaws 236, 238 are adjacent one another in the retracted position, the jaws 236, 238 together substantially cover the opening 108 of the elongate tube 102. Proximal edges of the jaws 236, 238 protrude distally from the proximal edge 110 of the beveled end region of the elongate tube 102, which can help to prevent coring of the patient's tissue as the suture passer is passed through the tissue. Furthermore, the jaws 236, 238 are sized such that a sufficient clearance remains between outer edges 240, 242 of the blocking jaws 236, 238 and an inner surface of the elongate tube 102. The remainder of the suture passer can have substantially the same structure and function as the suture passers described above. For example, the grasping member 504, can further include arms extending from proximal ends of the jaws 234, 236, 238, respectively, and a common base 244 extending from proximal end regions of the arms that is formed to engage with a distal end region of an internal rod included within the suture passer. A proximal end region of the internal rod is coupled to a plunger assembly housed within a handle, which is used to extend and retract the grasping member 504.

While the plunger assemblies of the suture passers described above are configured to bias the grasping members to the retracted position, the plunger assemblies can alternatively be configured to bias the grasping members to the extended position.

While the plunger assemblies of the suture passers described above are configured to bias the grasping members in a certain axial direction, in some embodiments, the plunger assemblies are configured so that the grasping members are not biased. In such embodiments, for example, the grasping member can be extended by depressing the button of the plunger assembly and can be retracted by pulling the button of the plunger assembly.

While the wound repair procedures described above and using the suture passer 100 have been described with respect to laparoscopic surgeries, the suture passer 100 can be used to repair wounds resulting from the use of endoscopic ports in other types of endoscopic surgeries. Additionally, the suture passer 100 can be used to close wounds created during certain surgical procedures where it is desirable to pass a suture through a ligament without coring the ligament, such as vaginal, sacrospinous, and uterosacral ligament suspension surgeries.

What is claimed is:

1. A suture passer comprising:
   an elongate tube defining a central lumen, the elongate tube having a beveled distal end that lies within a plane and an opening defined by the beveled distal end, the opening lying fully within the plane; and
   a grasping member comprising a first elongate member and a first jaw, the first jaw extending distally from the first elongate member, the first jaw defining a planar surface that extends laterally with respect to the first elongate member, the first jaw having a width greater than a width of the first elongate member, the grasping member sized to be disposed within the elongate tube, the grasping member capable of being extended from the elongate tube in a manner such that the first elongate member and the first jaw are disposed at least partially distal to the beveled distal end of the elongate tube, and the grasping member capable of being retracted within the elongate tube in a manner such that the first elongate member is located substantially within the central lumen of the elongate tube and the planar surface of the first jaw is oriented parallel to the plane in which the beveled distal end and the opening lie, such that the planar surface of the first jaw substantially covers the opening defined by the beveled distal end of the elongate tube.

2. The suture passer of claim 1, wherein the first jaw covers about 80% to about 95% of an area of the opening.

3. The suture passer of claim 1, wherein the opening has an elliptical shape.

4. The suture passer of claim 3, wherein the first jaw has a substantially elliptical shape, such that the first jaw substantially covers the opening while the grasping member is retracted within the elongate tube.

5. The suture passer of claim 1, wherein the beveled distal end region of the elongate tube comprises a proximal edge and a distal edge.

6. The suture passer of claim 5, wherein the first jaw includes a first edge and a second edge, the first edge being aligned substantially flush with the distal edge of the beveled distal end of the elongate tube when the grasping member is retracted within the elongate tube, and the second edge protruding distally from the proximal edge of the beveled distal end of the elongate tube when the grasping member is retracted within the elongate tube.

7. The suture passer of claim 6, wherein the second edge of the first jaw prevents the proximal edge of the elongate tube from coring a surgical wall as the suture passer is passed through the surgical wall.

8. The suture passer of claim 6, wherein the second edge protrudes distally from the proximal edge of the beveled distal end by about 0 inch to about 0.050 inch.

9. The suture passer of claim 1, further comprising a second elongate member and a second jaw extending distally from the second elongate member.

10. The suture passer of claim 9, wherein the first and second jaws cooperate to cover the opening when the grasping member is retracted within the elongate tube.

11. The suture passer of claim 10, wherein the first and second jaws cover about 80% to about 95% of an area of the opening when the grasping member is retracted within the elongate tube.

12. The suture passer of claim 9, wherein the first and second elongate members are laterally spaced apart.

13. The suture passer of claim 9, wherein the first and second elongate members are configured such that a suture can be captured between the first and second elongate members when the grasping member is retracted within the elongate tube.

14. The suture passer of claim 9, wherein the first elongate member includes a first bend from which the first jaw extends, the second elongate member includes a second bend from which the second jaw extends, and the first bend is longitudinally spaced from the second bend.

15. The suture passer of claim 14, wherein the first and second bends are arranged such that the second jaw contacts a central region of the first jaw when the grasping member is retracted within the elongate tube.

16. The suture passer of claim 14, wherein the first bend is spaced about 0.05 inch to about 0.125 inch from the second bend.

17. The suture passer of claim 14, wherein the first bend has a first bend radius, the second bend has a second bend radius, and the first bend radius is different than the second bend radius.

18. The suture passer of claim 17, wherein either or both of the first and second bend radii are about 0.050 inch to about 0.125 inch.

19. The suture passer of claim 1, wherein a peripheral edge of the first jaw is spaced from an inner surface of the elongate tube by about 0.005 inch to about 0.020 inch.

20. The suture passer of claim 19, wherein a space between the peripheral edge and the inner surface of the elongate tube is less than a thickness of a suture to be carried by the suture passer.

21. The suture passer of claim 1, wherein the grasping member further comprises a base connected to a proximal end of the first elongate member.

22. The suture passer of claim 21, wherein the base and the first elongate member are formed from a unitary structure.

23. The suture passer of claim 1, wherein the suture passer further comprises an internal rod disposed within the central lumen of the elongate tube and coupled to the grasping member.

24. The suture passer of claim 23, further comprising a plunger assembly coupled to a proximal end of the internal rod, the plunger assembly being operable to extend the grasping member from the beveled distal end of the elongate tube.

25. The suture passer of claim 24, wherein the plunger assembly is operable to retract the grasping member within the central lumen of the elongate tube.

26. The suture passer of claim 24, wherein the plunger assembly comprises a button, a plunging member, and a spring surrounding the plunging member.

27. The suture passer of claim 26, wherein the plunger assembly is spring-loaded such that the grasping member is retracted within the elongate tube while the button is released and the spring is extended, and the grasping member is extended distally from the beveled distal end of the elongate tube while the button is depressed and the spring is compressed.

28. The suture passer of claim 1, wherein the grasping member has a length of about 1.25 inches to about 8.5 inches.

29. The suture passer of claim 1, wherein the suture passer has a length of about 9 inches to about 11 inches.

30. The suture passer of claim 1, wherein the elongate tube has an outer diameter of about 0.060 inch to about 0.125 inch.

31. The suture passer of claim 1, wherein the elongate tube has an inner diameter of about 0.050 inch to about 0.110 inch.

* * * * *